(12) United States Patent
Kholoburdin et al.

(10) Patent No.: US 12,144,655 B2
(45) Date of Patent: Nov. 19, 2024

(54) METHOD AND DEVICE FOR LIVENESS DETECTION

(71) Applicant: Samsung Electronics Co., Ltd., Suwon-si (KR)

(72) Inventors: Viacheslav Sergeevich Kholoburdin, Tambov (RU); Vladislav Valerievich Lychagov, Saratov (RU); Dmitrii Igorevich Chernakov, Cherepovets (RU); Kirill Gennadievich Beliaev, St. Petersburg (RU); Dmitriy Alexandrovich Shelestov, Kotelniki (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 184 days.

(21) Appl. No.: 17/939,626

(22) Filed: Sep. 7, 2022

(65) Prior Publication Data
US 2023/0058966 A1    Feb. 23, 2023

Related U.S. Application Data

(63) Continuation of application No. PCT/KR2022/012274, filed on Aug. 17, 2022.

(30) Foreign Application Priority Data

Aug. 23, 2021  (RU) .............................. 2021124869

(51) Int. Cl.
*A61B 5/00* (2006.01)
*A61B 5/026* (2006.01)

(52) U.S. Cl.
CPC .......... *A61B 5/7221* (2013.01); *A61B 5/0261* (2013.01); *A61B 5/7246* (2013.01); *A61B 5/725* (2013.01); *A61B 2562/0242* (2013.01)

(58) Field of Classification Search
CPC ..... A61B 5/117; A61B 5/7221; A61B 5/0261; A61B 5/7246; A61B 5/725; A61B 2562/0242; G01S 7/415; G06V 40/45
See application file for complete search history.

(56) References Cited

U.S. PATENT DOCUMENTS 4,590,948 A    5/1986  Nilsson
4,596,254 A    6/1986  Adrian et al.
(Continued)

FOREIGN PATENT DOCUMENTS

CA    1 235 223 A    4/1988
CA    2 617 001 A1   7/2009
(Continued)

OTHER PUBLICATIONS

Russian Search Report dated Feb. 28, 2022, issued in Russian Patent Application No. 2021124869.
(Continued)

*Primary Examiner* — Keith M Raymond
*Assistant Examiner* — Johnathan Maynard
(74) *Attorney, Agent, or Firm* — Jefferson IP Law, LLP

(57) ABSTRACT

A live subject tissue detection device includes a light source configured to emit light onto the tissue of a subject, a photodetector configured to receive light reflected from the tissue and light reflected from the blood flow, wherein the light reflected from the blood flow has a Doppler shift relative to the light reflected from the tissue, and generate a high frequency Doppler signal based on the Doppler shift, a detection circuitry configured to receive the high frequency Doppler signal from the photodetector and convert the high frequency Doppler signal into a low frequency signal, and at least one processor configured to compute parameters of the low frequency signal, compare the parameters of the low
(Continued)

frequency signal to respective reference values, and determine a presence of live tissue based on the comparison.

20 Claims, 3 Drawing Sheets

(56) References Cited

U.S. PATENT DOCUMENTS

| | | | |
|---|---|---|---|
| 5,778,878 | A | 7/1998 | Kellam |
| 6,015,969 | A | 1/2000 | Nathel et al. |
| 6,173,197 | B1 | 1/2001 | Boggett et al. |
| 6,409,670 | B1 | 6/2002 | Yao et al. |
| 6,454,722 | B1 | 9/2002 | Numajiri et al. |
| 6,549,801 | B1 | 4/2003 | Chen et al. |
| 6,842,639 | B1 | 1/2005 | Winston et al. |
| 7,016,048 | B2 | 3/2006 | Chen et al. |
| 7,090,648 | B2 | 8/2006 | Sackner et al. |
| 7,359,062 | B2 | 4/2008 | Chen et al. |
| 7,894,046 | B2 | 2/2011 | Morofke et al. |
| 7,917,312 | B2 | 3/2011 | Wang et al. |
| 8,417,307 | B2 | 4/2013 | Presura et al. |
| 8,556,820 | B2 | 10/2013 | Alpert et al. |
| 9,031,640 | B2 | 5/2015 | Hachiga et al. |
| 9,618,824 | B2 | 4/2017 | Mohammed et al. |
| 10,695,086 | B2 | 6/2020 | Shabaz |
| 10,792,000 | B2 | 10/2020 | Jespersen et al. |
| 10,835,202 | B2 | 11/2020 | Haupt |
| 11,051,703 | B2 | 7/2021 | Liu et al. |
| 2005/0150309 | A1 | 7/2005 | Beard |
| 2008/0234590 | A1* | 9/2008 | Akkermans .......... A61B 5/0261 600/587 |
| 2009/0131791 | A1 | 5/2009 | Clark |
| 2009/0209871 | A1 | 8/2009 | Ueki et al. |
| 2014/0257075 | A1 | 9/2014 | Kagemann, Jr. et al. |
| 2018/0242844 | A1 | 8/2018 | Liu et al. |
| 2019/0005351 | A1 | 1/2019 | Zhou et al. |
| 2019/0082952 | A1 | 3/2019 | Zhang et al. |
| 2019/0095602 | A1 | 3/2019 | Setlak et al. |
| 2019/0125191 | A1* | 5/2019 | Siedenburg .......... A61B 5/6833 |
| 2019/0183358 | A1* | 6/2019 | Wakita ................ A61B 5/7203 |
| 2019/0298299 | A1 | 10/2019 | Kim et al. |
| 2021/0137385 | A1 | 5/2021 | De Haan |
| 2022/0229895 | A1* | 7/2022 | Ranjan ................ G06F 21/35 |

FOREIGN PATENT DOCUMENTS

| | | |
|---|---|---|
| CN | 101297217 A | 10/2008 |
| CN | 101325918 A | 12/2008 |
| CN | 105030223 A | 11/2015 |
| CN | 111772676 A | 10/2020 |
| CN | 112914538 A | 6/2021 |
| DE | 195 20 937 A1 | 1/1996 |
| JP | H11290300 A | 10/1999 |
| JP | 4506849 B2 | 7/2010 |
| KR | 10-2018-0031540 A | 3/2018 |
| KR | 10-2020-036281 A | 4/2020 |
| RU | 2019 132 487 A | 4/2021 |
| WO | 95/32664 A1 | 12/1995 |
| WO | 2002/026194 A2 | 4/2002 |
| WO | 2003/039364 A2 | 5/2003 |
| WO | 2007/023438 A2 | 3/2007 |
| WO | 2007/122375 A3 | 11/2007 |
| WO | 2008/103891 A2 | 8/2008 |
| WO | 2012/130249 A1 | 10/2012 |
| WO | 2012/156937 A1 | 11/2012 |
| WO | 2013/019845 A1 | 2/2013 |
| WO | 2017/027383 A1 | 2/2017 |
| WO | 2017/089479 A1 | 6/2017 |
| WO | 2017/143456 A1 | 8/2017 |

OTHER PUBLICATIONS

Russian Decision on Grant dated Jul. 11, 2022, issued in Russian Patent Application No. 2021124869.
International Search Report dated Dec. 5, 2022, issued in International Application No. PCT/KR2022/012274.

\* cited by examiner

[Fig. 1]
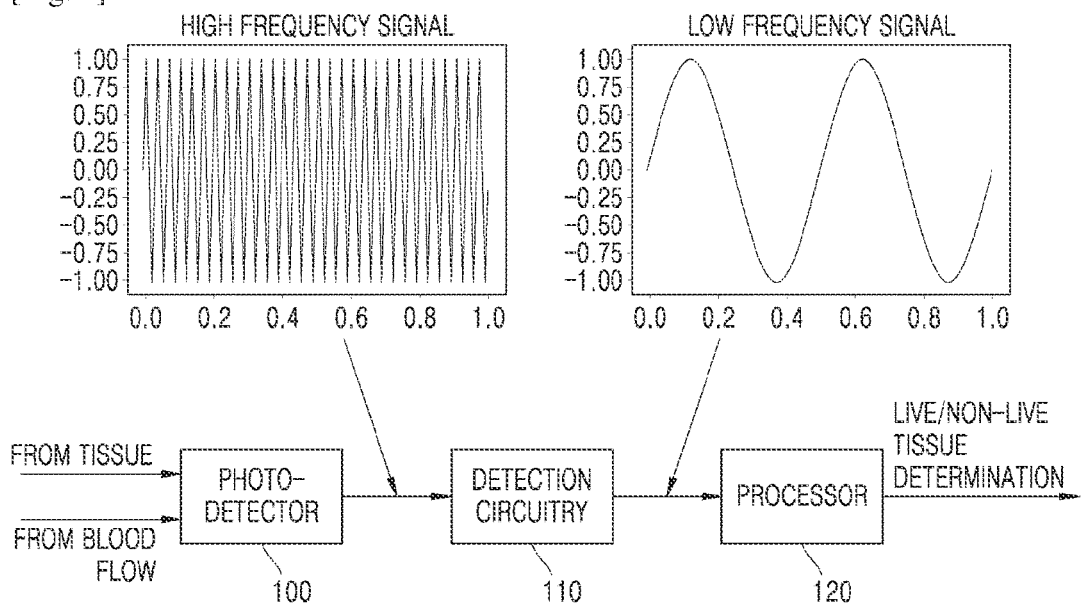
[Fig. 2]
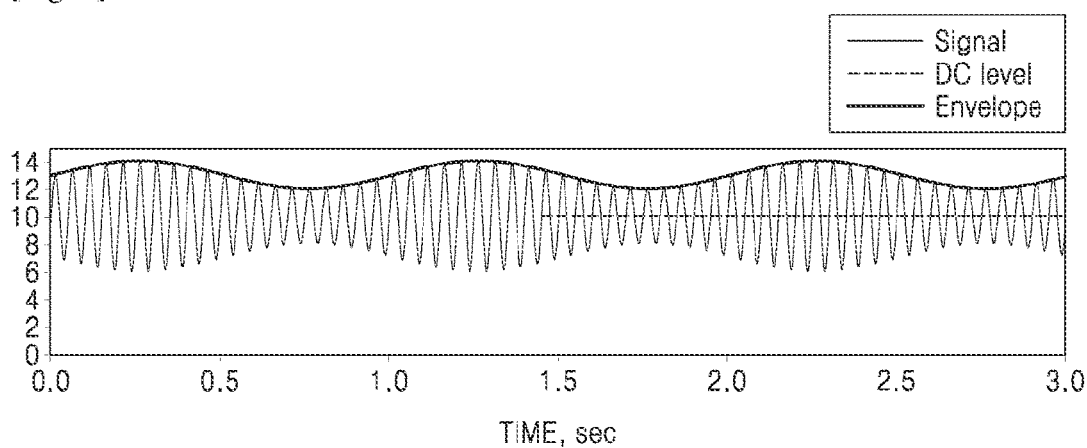

[Fig. 3]
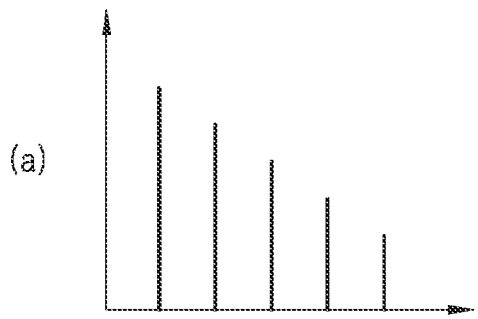
(a)
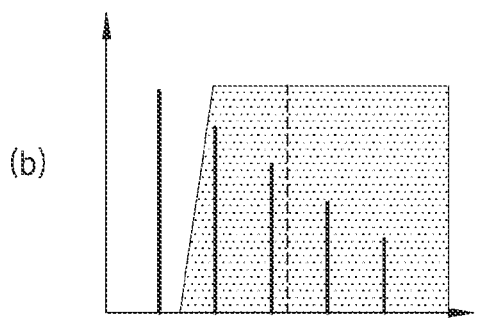
(b)
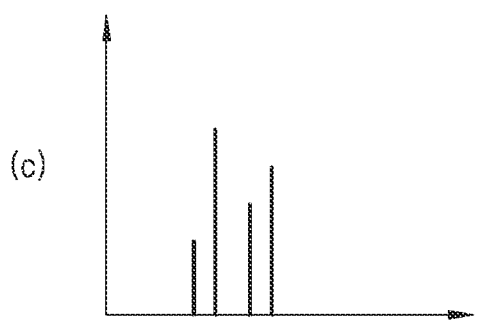
(c)

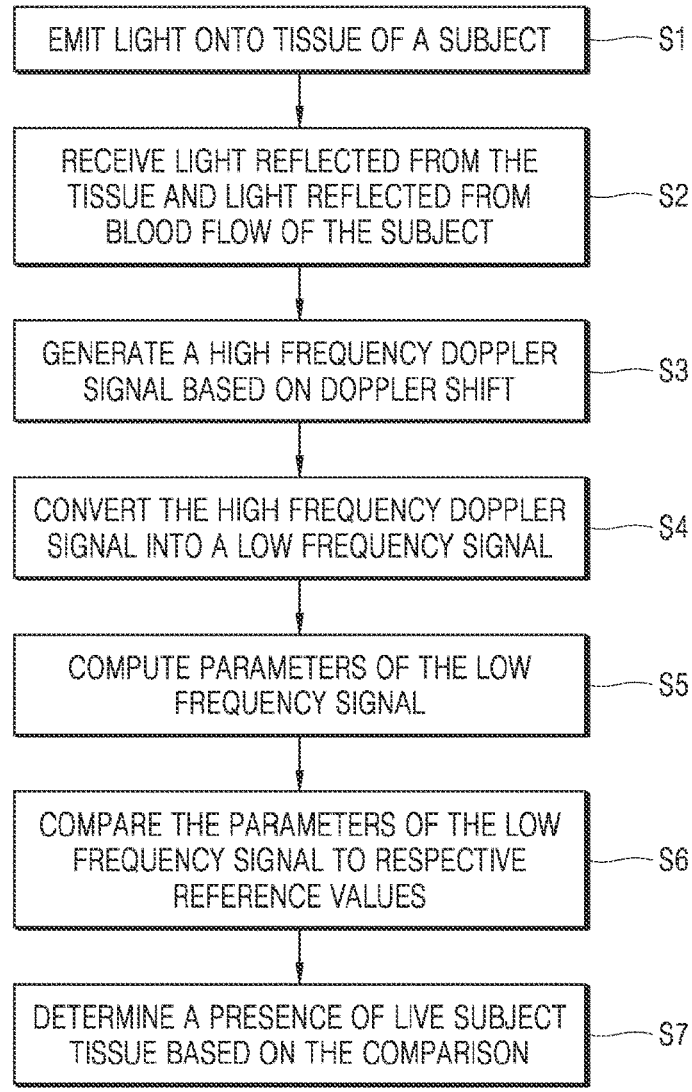
[Fig. 4]
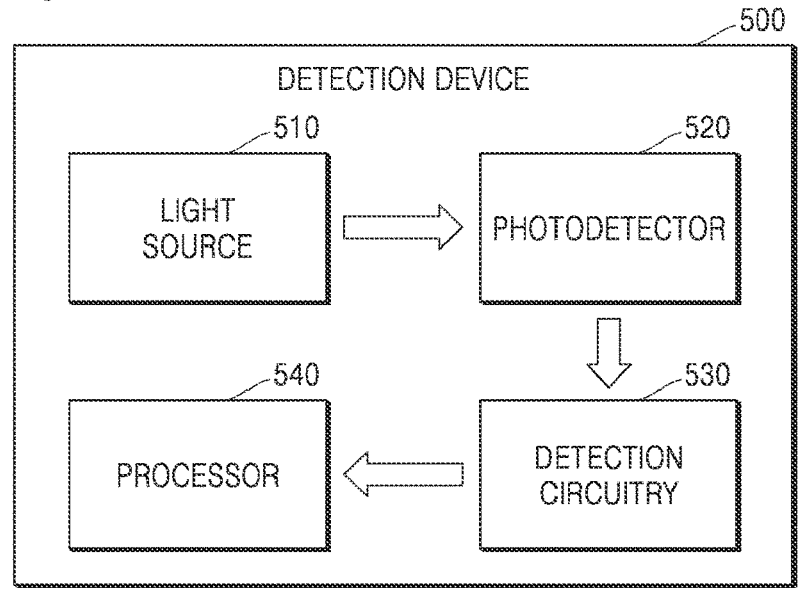
[Fig. 5]

METHOD AND DEVICE FOR LIVENESS DETECTION

CROSS-REFERENCE TO RELATED APPLICATION(S)

This application is a continuation application, claiming priority under § 365(c), of an International application No. PCT/KR2022/012274, filed on Aug. 17, 2022, which is based on and claims the benefit of a Russian patent application number 2021124869, filed on Aug. 23, 2021, in the Russian Intellectual Property Office, the disclosure of which is incorporated by reference herein in its entirety.

FIELD OF THE INVENTION

The disclosure relates to liveness measurement devices and, more particularly, the disclosure relates to a miniature measurement device (sensor) for contactless detection of live subject tissue (liveness) based on blood flow sensing by means of Laser Doppler Flowmetry (LDF).

PRIOR ART

At present, technologies for contactless live subject (user) tissue detection are actively developed, being used, in particular, in the design of wearable devices, such as, e.g., smart watches, electronic bracelets, etc. Subject liveness data obtained include, by way of a non-limiting example, heart rate (pulse), blood oxygen saturation, blood pressure data, etc. A live tissue detection device that implements such technologies has different fields of use, in particular in medicine (for remote monitoring of a subject's vital signs), sports (to determine different parameters related to a subject's physical activity), and for different purposes related to determining that a user is wearing the wearable device on their respective body part.

Current techniques for contactless live tissue and subject's liveness detection are based, in particular, on photoplethysmography (PPG). However, such techniques have a number of drawbacks, such as long response time, high energy consumption, notable artifacts caused, in particular, by subject's movement, and a possibility of "spoofing" the device as to whether the wearable device is being worn on a subject's respective body part.

Long response time in photoplethysmography-based techniques is caused by the fact that, when a PPG signal (i.e., a signal which reflects a subject's heartbeat) is used as a characteristic for the subject's liveness, presence/absence of a live subject tissue may be determined after monitoring the signal for at least 1-2 PPG signal periods. Taking into account that normally human heart rate is 60-100 per minute, minimum monitoring time should be 0.6 to 2 seconds. However, device users tend to regard such time interval as too long.

A normal light-emitting diode for PPG consumes 10-100 mA. Due to high energy consumption, operation time of a respective sensor should be minimized, which is bad, in particular, for the uses of the sensor, which are related to security measures.

Motion artefacts reduce the accuracy of live subject tissue detection using PPG. Besides, since the PPG signal substantially only reflects a higher or lower intensity of light that is reflected back to the detector, the PPG sensor may be easily "spoofed" by simulating heartbeat through back-and-forth movement of a reflective object under the sensor.

Reference U.S. Pat. No. 6,173,197 (Moor Instruments Limited, published 09.01.2001) discloses an apparatus for measuring microvascular blood flow in tissue including a monochromatic light source to irradiate a section of a subject's body tissue with the monochromatic light, a photodetector to collect light scattered from the irradiated section, at least one processor for processing the electrical output signals from the photodetector, calculating the power spectrum of photocurrents generated in the detection of laser light scattered from static tissue and Doppler broadened laser light scattered from moving blood cells, and recording the average Doppler frequency shift. The apparatus further measures and records the intensity of the detected scattered light, filters out movement artefact noise. This related art solution is substantially a basic design for Laser Doppler Flowmetry (LDF). Among drawbacks of this related art solution is that it requires using a complex probing system.

Reference WO 2007/122375 (THE UNIVERSITY OF NOTTINGHAM, published 01.11.2007) discloses a photoplethysmography (PPG) device which includes a light source for illuminating a target object. A modulator drives the light source such that the output light intensity varies as a function of a modulation signal at a modulation frequency. A detector receives light from the target object and generates an electrical output signal as a function of the intensity of received light. A demodulator with a local oscillator receives the detector output signal and produces a demodulated output signal representative of the modulation signal. The demodulator is insensitive to any phase difference between the modulation signal and the oscillator of the demodulator. Based on the demodulated output signal, a signal indicative of blood volume as a function of time and/or blood composition is generated. A number of demodulators may be provided to derive signals from multiple light sources of different wavelengths, or from an array of detectors. The PPG device may operate in a transmission mode or a reflectance mode. When in a reflectance mode, the device may use the green part of the optical spectrum and polarizing filters. This solution is substantially a basic design for photoplethysmography (PPG). Among the drawbacks of this related art solution, one may mention the need for monitoring several signal periods (several heart beats) to detect a live tissue of a subject based on the heartbeat.

Reference US 2019/0095602 (Apple Inc., published 28.03.2019) discloses a method of authenticating a user of a wearable electronic device which includes emitting light into an upper side of a forearm near a wrist of the user; receiving, using a light field camera, reflected light from the upper side of the forearm of the user; generating a light field image from the reflected light; performing a synthetic focusing operation on the light field image to construct at least one image of at least one layer of the forearm surface near the wrist; extracting a set of features from the at least one image; determining whether the set of features matches a reference set of features; and authenticating the user based on the matching. In some embodiments, the method may further include compensating for a tilt of the light field camera prior to or while performing the synthetic focusing operation. In this related art solution, user authentication and live tissue detection make use of features from different focal planes. Among the drawbacks of this related art solution, one may mention a need for a compact light field camera, while currently no light field camera with such small size is commercially available.

Reference WO2008/103897 (Honeywell International Inc., published 28.08.2008) describes a device for detecting the presence of human tissue including an illuminator source for providing encoded light in a first and second IR bands, wherein the first band light is reflected from skin and the second band light is absorbed by the skin. A detector receives the light in said bands after having contacted with the skin and provides an encoded signal indicating the presence or absence of light in each of the frequency bands. A processing unit decodes the signal, processes it and indicates the presence of human tissue (skin) when the first IR band light is present and the second IR band light is absent. Thus, the related art solution provides for an analysis of transmittance and absorption of light in two optical spectrum frequency bands. Among drawbacks of this related art solution, one may mention a complex light receiver design and its operation being susceptible to artifacts caused by a subject's movement (hereinafter also referred to as motion artifacts).

Substantially, the task of detecting live tissue and also determining certain vital signs of a subject, as aforementioned, may be attended to using approaches on the basis of photoplethysmography (PPG) and Laser Doppler Flowmetry (LDF). As aforementioned, PPG-based techniques have drawbacks such as relatively slow operation (in particular, in order to judge on the presence/absence of a live tissue, it is necessary to monitor at least two heartbeats, i.e., it takes about 2 seconds). Unlike PPG, in LDF a signal is generated by detecting blood flow and not heartbeat, whereas a frequency at which the signal is generated is about 1000 times higher with LDF, which allows a significantly faster operation.

The above information is presented as background information only to assist with an understanding of the disclosure. No determination has been made, and no assertion is made, as to whether any of the above might be applicable as prior art with regard to the disclosure.

SUMMARY

This section which discloses various aspects and embodiments of the claimed disclosure is intended for providing a brief overview of the claimed subject matters and their embodiments. Detailed characteristics of technical means and methods that implement the combinations of features of the claimed disclosures are provided hereinbelow. Neither this summary of disclosure nor the detailed description provided below together with accompanying drawings should be regarded as defining the scope of the claimed disclosure. The scope of legal protection of the claimed disclosure is only defined by the appended set of claims.

Taking into account the prior art discussed above, the technical problem to be resolved by the claimed disclosure consists in providing a method and device for detecting a live subject tissue using the LDF technique, which would meet the following requirements:

eye safety for a subject,
low energy consumption,
small size of the device,
short response time (fast operation), and
high "signal to noise" ratio (SNR) while using a light source with low energy consumption.

Aspects of the disclosure are to address at least the above-mentioned problems and/or disadvantages and to provide at least the advantages described below. Accordingly, an aspect of the disclosure is to provide a compact sensor for detecting a live subject tissue with a short response time, which is resistant to motion artifacts and malicious manipulations with the device that includes the inventive sensor.

Technical result achieved by using the disclosure consists in highly accurate and fast detection of a live subject tissue. Besides, reliable security of using the wearable device in which the method and/or device are used, as well as accuracy of subject's vital signs measurement by the wearable device in which the method and/or device are used are achieved.

Additional aspects will be set forth in part in the description which follows and, in part, will be apparent from the description, or may be learned by practice of the presented embodiments.

In accordance with an aspect of the disclosure, —a live subject tissue (liveness) detection device is provided. The live subject issue includes a light source configured to emit light onto the subject' tissue, a photodetector configured to receive light reflected from the subject's tissue and light reflected from the subject's blood flow, wherein light reflected from the subject's blood flow has a Doppler shift relative to the light reflected from the subject's tissue, wherein the photodetector is configured to generate a high frequency Doppler signal based on said Doppler shift, a detection circuitry configured to receive the high frequency Doppler signal from the photodetector and to convert it into a low frequency signal, and at least one processor configured to determine the presence of a live tissue based on the low frequency signal from the detection circuitry by computing the low frequency signal parameters and comparing the computed low frequency signal parameters to respective reference values.

In one or more embodiments, the detection circuitry comprises an analog-to-digital converter configured for analog-to-digital conversion of the high frequency Doppler signal. The detection circuitry may be configured to mix light reflected from the subject's tissue and light reflected from the subject's blood flow. The detection circuitry may further comprise a low-pass filter, a high-pass filter, or a band-pass filter.

The light source may be embodied as a coherent light source, such as a laser diode. The photodetector may be embodied as a photo diode or a heterodyne detector.

In accordance with another aspect of the disclosure, a live subject tissue detection method is provided. The live subject tissue detection method includes the operations of emitting light onto the subject's tissue, receiving light reflected from the subject's tissue and light reflected from the subject's blood flow, wherein light reflected from the subject's blood flow has a Doppler shift relative to the light reflected from the subject's tissue, generating a high frequency Doppler signal based on said Doppler shift, converting the high frequency Doppler signal into a low frequency signal, computing the low frequency signal parameters and comparing the computed low frequency signal parameters to respective reference values, and determining the presence or absence of a live subject tissue based on said comparison.

In one or more embodiments, converting the high frequency Doppler signal into a low frequency signal comprises performing an analog-to-digital conversion of the high frequency Doppler signal into the low frequency signal. The analog-to-digital conversion of the high frequency Doppler signal may comprise generating an envelope of the high frequency Doppler signal.

In one or more embodiments, the high frequency Doppler signal is obtained by mixing light reflected from the subject's tissue and light reflected from the subject's blood flow. Converting the high frequency Doppler signal into a low frequency signal may comprise at least one of performing a high-pass filtering on the high frequency Doppler signal, performing a low-pass filtering on the high frequency Doppler signal, and performing a band-pass filtering on the high frequency Doppler signal.

In yet another aspect of the disclosure, the above-mentioned object is achieved by a wearable user device comprising a live subject tissue detection device according to the above-mentioned first aspect.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 shows a schematic diagram of operation of the live subject tissue detection device according to an embodiment of the disclosure;

FIG. 2 shows a diagram which illustrates a Laser Doppler Flowmetry (LDF) signal obtained in the live subject tissue detection device according to the according to an embodiment of the disclosure;

FIG. 3 shows diagrams which illustrate frequency aliasing in one or more according to an embodiment of the disclosure; and FIG. 4 shows a flow chart of a method according to an embodiment of the disclosure.

FIG. 5 shows a block diagram illustrating an example configuration of an live subject tissue detection device according to an embodiment of the disclosure.

The same reference numerals are used to represent the same elements throughout the drawings.

DETAILED DESCRIPTION OF EMBODIMENTS

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The disclosure is based on using a Laser Doppler Flowmetry (LDF) sensor for detecting a live subject tissue. In general, the principle of operation of the LDF sensor is based on illuminating a portion of a subject's skin with a laser and analyzing interference properties between light scattered by the blood flow and light scattered by surrounding tissues.

In the disclosure, the term "blood flow" generally means a process of blood cells' movement. This movement is characterized, firstly, by a characteristic blood velocity in human capillaries (the Doppler shift being directly dependent on this velocity) and, secondly, by a total power of light scattered by the cells (the amount of blood influences the signal amplitude). Due to the parameters of the blood flow velocity and blood amount being quite specific, the signal received from blood cells has a characteristic pattern (unlike micromotions, blood flow and amount in a wrist are quite constant), which makes it simpler to distinguish the blood flow from the movement or flow of other physiological fluids. E.g., when muscles move, a quite large mass of tissue moves as a whole, and velocity of such movement is not constant, while, for moving lymph, its amount and, more particularly, its velocity significantly differs from the same parameters of the blood, by virtue of which the signal amplitude and Doppler shift for muscles and lymph are significantly different.

As a rule, LDF is used in medical appliances for precise measurement (<1%) of a subject's blood flow parameters (in particular, blood flow velocity), which is implemented using high stability lasers, specialized analog-to-digital converters, etc. Respective medical appliances are characterized by high complexity, large dimensions and high energy consumption. There are more miniature wearable devices which are specially intended for remote monitoring of subjects' blood flow velocity. The claimed disclosure concentrates on resolving the task of detecting live tissue and, in some non-limiting embodiments, also on measuring a subject's heart rate. For this purpose, the claimed disclosure is implemented in a miniature sensor, dimensions and energy consumption of which allow embedding the sensor in multi-functional wearable devices, such as, by way of a non-limiting example, smart watches, electronic bracelets, etc.

To achieve this object, the claimed disclosure has been optimized as compared to prior art LDF-based solutions which are used in medicine. The claimed disclosure does not require precise blood flow velocity measurements, and the data generated in the disclosure should be substantially sufficient for a fast judgment whether a tissue is a live one or not a live one.

FIG. 1 shows a schematic diagram of operation of the live subject tissue detection device according to an embodiment of the disclosure.

Referring to FIG. 1, in the first aspect the disclosure is implemented as a live subject tissue detection device comprising a light source, a photodetector 100, a detection circuitry 110, and at least one processor 120.

The light source is configured to emit light onto a subject's tissue, thus illuminating a portion of a subject's tissue, such as, by way of a non-limiting example, a wrist area if the device is implemented in a wearable user device, such as a smart watch or an electronic bracelet. By way of a non-limiting example, the light source may be a laser diode configured to emit coherent light with a wavelength in the range of about 630 to about 860 nm, preferably about 850 nm. As an alternative, the light source may be embodied as any other source of coherent light, such as a crystalline laser, a fiber based source, a gas based source, etc.

Coherent light emitted by the light source onto a subject's tissue is reflected from the subject's skin and blood flow (blood cells flow through blood vessels). As such, light reflected from the subject's blood flow has a Doppler shift relative to the light reflected from the subject's tissue. This Doppler shift is substantially a feature which distinguishes live tissue from any other ("non-live") surface in accordance with the concept. In case of a "non-live" surface all coherent light would be reflected from the surface without said Doppler shift.

The photodetector 100 is configured to receive (detect) light reflected from the subject's tissue, and light reflected from the subject's blood flow. Besides, the photodetector 100 is configured to detect the Doppler shift of the light reflected from the subject's blood flow relative to the light reflected from the subject's tissue. In the context of the disclosure, the Doppler shift of the light reflected from the subject's blood flow is expressed by a certain shift in frequency and/or wavelength of light reflected from the subject's blood flow relative to the light reflected from the subject's tissue. As such, light reflected from the subject's tissue returns to the photodetector 100 with substantially the same frequency and/or wavelength, with which it was emitted. This is due to the fact that tissue may be considered substantially as a surface at rest, while the blood flow is characterized by blood cells' movement through blood vessels, which is further influenced, in particular, by the subject's heartbeat.

Light reflected from the subject's tissue and light reflected from the subject's blood flow are subjected to interference in the photodetector 100, whereby the photodetector 100 outputs an electric signal in a band that corresponds to the frequency difference between the light reflected from the tissue and the light reflected from the blood flow.

Thus, based on the detected Doppler shift, the photodetector 100 is configured to output an electric signal, which is further referred to as a high frequency Doppler signal. Said high frequency Doppler signal has a frequency, by way of a non-limiting example, in the range of about 1 to about 10 kHz, which generally corresponds to a frequency of oscillations generated by the subject's blood flow. High frequency Doppler signal in the context of the disclosure is illustrated in FIG. 2.

FIG. 2 shows a diagram which illustrates a Laser Doppler Flowmetry (LDF) signal obtained in the live subject tissue detection device according to an embodiment of the disclosure.

In one or more non-limiting embodiments of the disclosure, the high frequency Doppler signal is obtained in the photodetector 100 by mixing light reflected from the subject's tissue and light reflected from the subject's blood flow. In one or more non-limiting embodiments, the photodetector may be embodied as a photodiode or a heterodyne detector. As an alternative, the photodetector 100 may be embodied as a photo resistor and a photo transistor.

Referring to FIG. 1, a detection circuitry 110 is configured to receive a high frequency Doppler signal from a photodetector 100 and to convert it into a low frequency signal, in particular, by means of frequency aliasing from the high frequency band (1 to 10 kHz as aforementioned) into a low frequency band (by way of a non-limiting example, approximately less than 1 kHz), and analog-to-digital conversion of the signal. For this purpose, in one or more non-limiting embodiments, the detection circuitry 110 comprises a high-pass filter and a low frequency analog-to-digital converter.

First, the high frequency Doppler signal is filtered to remove the low frequency component (by way of a non-limiting example, the component with a frequency lower than ½ of sampling frequency Fs (in other words, Fs/2)).

Signal sampling is performed by means of the analog-to-digital converter with a sampling frequency Fs. The sampling allows a frequency aliasing, when the filtered high frequency component with a frequency F>Fs/2 is reflected relative to the sampling frequency Fs into the low frequency region with a frequency Fnew=Fs−F. This makes it possible to analyze the signal which substantially corresponds to the high frequency Doppler signal, in a low frequency band (approximately 1 kHz as aforementioned), which is less computationally expensive as compared to an analysis of the high frequency signal per se without said frequency aliasing into a low frequency band, but still provides a sufficient amount of data, obtained in the form of a high frequency Doppler signal, at least to achieve the main object, i.e., live tissue detection.

FIG. 3 shows diagrams which illustrate frequency aliasing in one or more according to an embodiment of the disclosure.

Referring to FIG. 3, frequency aliasing in the context of the disclosure is illustrated in the diagrams. Diagram A shows signal levels for all frequencies in the input signal. In diagram B, the dashed area shows the region of the frequency spectrum which passes through the high-pass filter, and the thin vertical line shows a sampling frequency. In diagram C, the result of frequency aliasing over the sampling frequency is shown.

The low frequency component being removed is substantially low frequency noise resulting, by way of a non-limiting example, from the movement of a subject's hand, on which the wearable device that implements the disclosure is worn by the subject. This allows canceling motion artifacts, thus improving the accuracy of live tissue detection.

The low frequency (digital) signal resulting from said analog-to-digital conversion is transmitted to the at least one processor 120, where parameters of the low frequency signal are computed, based on which the presence or absence of live tissue is eventually determined.

The at least one processor 120 is configured to determine the presence of a live tissue based on the low frequency signal from the detection circuitry by computing the parameters of the low frequency signal and comparing the computed parameters of the low frequency signal to respective reference values.

In one or more non-limiting embodiments, low frequency sampling of the high frequency Doppler is performed using generating an envelope of the high frequency Doppler signal as shown in FIG. 2 for further measuring the heartbeat rhythm.

In some non-limiting embodiments of the disclosure, the high-pass filter may be omitted, or a low-pass filter may be used instead. Such embodiments are suitable, in particular, for implementing the disclosure in particularly miniature wearable devices, such as, by way of a non-limiting example, fitness bracelets. Absence of a high-pass filter would retain the noise component, caused by mechanical movements of the device, in the signal input to the low frequency analog-to-digital converter but would make it possible to obtain certain additional information in case of proper signal processing in the at least one processor, said additional information characterizing, in particular, the subject's vital signs and/or psychoemotional status.

Besides, in certain embodiments of the disclosure, instead of the high-pass filter, a band-pass filter may be used, which is configured to cancel components at all frequencies other than the specific frequencies of interest, in particular other than the frequencies which are close to those which are characteristic for a subject's blood flow. This, in particular, provides for an improved signal-to-noise ratio (SNR), however it requires more complex and, possibly, bulkier filter electronics.

The processing of a signal received from the low frequency analog-to-digital converter by the at least one processor is carried out in accordance with the following sequence of operations.

After digitizing (analog-to-digital conversion), a direct current level of signal (DC level) is calculated for the signal received by the at least one processor 120, and the signal spectrum is calculated, in particular signal power levels in one or more different spectral bands are calculated.

In this context, the DC level of the signal is a signal from the photodiode, averaged over a long time (much longer than the characteristic period of LDF, e.g., 100 milliseconds). Such averaging shows the general power of the reflected signal and allows singling out objects which significantly differ from human skin in their reflectance (e.g., such as metals).

Further, said signal power levels in the one or more different spectral bands and the DC level are compared to respective reference (threshold) values, which are predefined for the respective levels. If said signal power levels in the one or more different spectral bands and the DC level are greater than respective reference (threshold) values, it is determined that tissue adjacent to the live tissue detection device is live tissue, i.e., belongs to a live subject. If said signal power levels in the one or more different spectral bands and the DC level are lower than the respective reference (threshold) values, it is determined that the tissue adjacent to the live tissue detection device is a non-live material.

Reference threshold values are selected by means of a machine learning technique based on a large set of collected and processed data for live and non-live subjects. Threshold values are selected so as to provide the most reliable live tissue sensing with a minimum level of false determinations for a non-live tissue. For example, for a prototype of the sensor, the signal power in a 450-500 Hz frequency band should be $5.4*10-14-1.7*10-12$ Watt.

In one or more embodiments of the disclosure, instead of signal DC level measurement a low dynamic range signal may be detected (measured). This allows determination of whether the signal input to the at least one processor is within the dynamic range of the device. If the signal input in the at least one processor is beyond the dynamic range of the device (i.e., below the lower threshold or above the higher threshold of a preset dynamic range), it may be stated that the tissue adjacent to the live tissue detection device is a non-live material. In this particular embodiment of the device, a relatively low computational complexity is involved, by virtue of which a less powerful at least one processor circuitry may be used, and the device may be readily integrated into existing wearable devices.

In one or more embodiments of the disclosure, after comparing the signal power levels in one or more different spectral bands and the signal DC level to respective reference (threshold) values, a so-called "sliding window" algorithm which makes it possible to flexibly adjust the requirements to subjects' live tissue detection by the device depending on the environmental conditions and/or specific current scenario of the live tissue detection device. By way of the non-limiting example, requirements for live subject tissue detection may vary depending on the current mode of operation of the wearable device, in which the device is integrated. So, e.g., in one mode the determination as to the tissue adjacent to the live tissue detection device being a live subject tissue may be made if, within a predefined time period (by way of a non-limiting example, 10 seconds) the device indicates the presence of a live subject tissue, e.g., within 99% of this time period. In another mode, for a determination that a tissue adjacent to the live tissue detection device is a live subject tissue it may be sufficient if the device indicates the present of a live subject tissue, e.g., within 70% or 80% of the same or different preset time period. In such particular embodiment of the disclosure, additional flexibility of use of the device in different modes of operation of the wearable device may be provided, e.g., for ensuring additional security or convenience of use of the device for a user. Besides, in such an embodiment of the disclosure, additional robustness of operation of the device against motion artifacts is provided, however in this case response time of the device is longer as compared to other embodiments.

Besides, in one or more particular embodiments of the disclosure, the processor may not use the determination of signal DC level. This allows using certain filters before the analog-to-digital conversion of the signal, however this complicates the algorithm of live or non-live tissue determination based on the comparison of signal power in one or more spectral bands to respective threshold values. In particular, in such embodiments, a band-pass filter or a high-pass filter may be employed, which may cancel both the low frequency component and the signal DC level from the filtered signal. Thus, the determination of live or non-live tissue may only make use of power values of respective spectral bands of the signal, which entails the need for using a more complicated algorithm. In particular, such embodiment of the disclosure is suitable for the cases where a high signal-to-noise ratio (SNR) is necessary, in view of which it is necessary to employ, e.g., a band-pass filter prior to analog-to-digital conversion of the signal.

In one or more embodiments of the disclosure, after the analog-to-digital conversion of the signal, the processor may be configured for further processing of the signal to acquire other data besides live/non-live tissue determination. By way of a non-limiting example, from the signal digitized at a frequency about 1 kHz as aforementioned, data on heart rate, blood pressure, cardiovascular system status, subject's psychoemotional status, etc., may be obtained. These parameters are computed using machine learning techniques (e.g., neural networks) from a received raw signal. For example a neural network is trained using a large set of marked-up data, in which there are data for people with different blood pressure values. Parameters with which the neural network operates may be, e.g., a difference between the maximum and minimum signal values, mean noise (RMS), signal increase rate at pulse, etc.

For this purpose, adjusting the position of the device may be further required, in view of which a possibility of requesting a user of the wearable device, in which the device is integrated, e.g., to put the device adjacent to one of the arteries of the subject's hand, through the user interface of the wearable device may be provided.

In one or more embodiments, the light source and/or photodetector may be supplemented by optical light focusing/collection means, such as, by way of a non-limiting example, lenses, Fresnel lenses, diffractive optical elements (DOEs). This makes it possible to further improve the efficiency of penetration of the light emitted by the light source into the tissue for detecting blood flow, and/or gathering light reflected from the tissue surface and/or the subject's blood flow, respectively. Besides, in this way, penetration of light emitted by the light source into the subject's tissue to a predetermined depth may be achieved. This allows an increase in the intensity of the collected reflected light and/or the signal to noise ratio (SNR) of the signal, but it requires the provision and alignment of additional optical system components.

FIG. 4 shows a flow chart of a method according to an embodiment of the disclosure.

Referring to FIG. 4, a method for live subject tissue detection, carried out by the device (sensor) is further explained. It should be noted that the method is implemented in the live tissue detection device (sensor) integrated in a wearable user device, such as, by way of a non-limiting example, smart watch, fitness bracelet, ring, etc. However, it should be understood that this list of wearable devices, in which the method is implemented, is not exhaustive, and the disclosure may also be implemented in more specialized wearable user electronic devices, such as, e.g., a diving computer, wearable devices for action sports, etc. Besides, it shall be understood that the disclosure may be implemented in both legacy wearable user devices, e.g., by integration in a structure of legacy smart watch, electronic bracelet, etc., and in devices which may be designed in the future.

At operation S1, light is emitted onto a subject's tissue. For this purpose, a light source is used, which is configured to emit light onto a subject's tissue, thus illuminating a portion of a subject's tissue, such as, by way of a non-limiting example, a wrist area located under a wearable device worn on a user's forearm. By way of a non-limiting example, the light source may be a laser diode configured to emit coherent light.

At operation S2, light reflected from the subject's tissue, and light reflected from the subject's blood flow are received, wherein the light reflected from the subject's blood flow has a Doppler shift relative to the light reflected from the subject's tissue. For this purpose, a photodetector (photodiode) is used, which has been described above in relation to the device.

At operation S3, based on the Doppler shift, the photodetector generates a high frequency Doppler signal, which is provided to a detection circuitry according to the disclosure. In one or more embodiments of the disclosure, the Doppler shift may be obtained by mixing the light reflected from the subject's tissue with the light reflected from the subject's blood flow.

At operation S4, high frequency Doppler signal is converted into a low frequency signal in the detection circuitry. This conversion is performed, in particular, by frequency aliasing from the high frequency band (1 to 10 kHz as aforementioned), which corresponds to the high frequency Doppler signal, to a low frequency band (by way of a non-limiting example, approximately less than 1 kHz). Then analog-to-digital conversion of the signal is performed.

Besides, in some embodiments operation S4 may comprise at least one sub-operation, at which the high frequency Doppler signal is filtered to cancel the low frequency component (by way of a non-limiting example, a component with a frequency lower than ½ of sampling frequency Fs (in other words, Fs/2)), wherein the high frequency component with frequency F>Fs/2 is aliased relative to the sampling frequency Fs to a low frequency band with frequency Fnew=Fs−F.

At operation S5, parameters of the low frequency signal are computed, based on which the presence or absence of the live tissue is judged. For this purpose, the processor as described above is used, which receives the low frequency (digital) signal from the detection circuitry. As aforementioned, this parameter computation may comprise, in particular, determining the direct current (DC) level of the signal and the signal power in one or more specific frequency bands.

At operation S6, the processor compares the computed parameters of the low frequency signal with respective reference values. As the reference values, in particular, preset threshold values of the DC level of the signal and signal power in the one or more specific frequency bands may be used.

At operation S7, the processor determines the presence or absence of the live subject tissue based on said comparison of the computed parameters of the low frequency signal with respective reference values.

FIG. 5 shows a block diagram illustrating an example configuration of an live subject tissue detection device according to an embodiment of the disclosure. As shown in FIG. 5, the live subject tissue detection device 500 includes a light source 510, a photodetector 520, a detection circuitry 530, and at least one processor 540. The light source 510 can emit light onto a tissue of a subject. The photodetector 520 can receive light reflected from the tissue of the subject and light reflected from the blood flow of the subject. The detection circuitry 530 can receive the high frequency Doppler signal from the photodetector 520, and convert the high frequency Doppler signal into a low frequency signal. The at least one processor 540 can compute parameters of the low frequency signal, compare the parameters of the low frequency signal to respective reference values and determine a presence of live subject tissue based on the comparison.

Practical implementation of the method and device according to the disclosure has demonstrated the possibility of implementation of the intended use of the disclosure (live subject tissue detection) and the achievement of the technical result (highly accurate and fast detection of a live subject tissue). In one of the practical implementations of the disclosure, the live subject tissue detection device was integrated in a wearable user electronic device, namely in a Samsung smart watch. The device comprised a light source embodied as a laser diode, a photodetector embodied as a photodiode, a detection circuitry including a low-pass filter and a low frequency analog-to-digital converter, and at least one processor embodied as an application-specific integrated circuit (ASIC).

It should be noted that the processor implemented in the form of an ASIC does not restrict the scope of the claimed disclosure, and the processor may also be used in the form of an integrated processor of the wearable device (e.g., an advanced reduced instruction set computer (RISC) machine (ARM)), at least one general purpose processor under control of an appropriate program stored in a computer-readable medium, and/or firmware, at least one microprocessor, etc. Different implementations of the processor suitable for use in the disclosure will be apparent to those skilled in the art.

The photodetector output an electric signal that corresponded to the detected Doppler shift between the light reflected from the tissue and the light reflected from the subject's blood flow, with a frequency in the range of approximately 1 to approximately 10 kHz, which generally corresponded to the frequency of vibrations generated by the subject's blood flow.

The signal was sampled by the low frequency analog-to-digital converter with frequency aliasing in which the filtered high frequency component was aliased relative to the sampling frequency into the low frequency band.

The processor implemented a processing algorithm which included the operations of calculating the spectrum of the digitized low frequency signal, measuring the direct current level of the signal, splitting the low frequency signal into three spectral bands, determining the total signal power in each of the three spectral bands, and comparing the signal power levels in each of the three spectral bands and the DC level of the signal with respective preset threshold values.

The device has been tested in several use scenarios. In particular, the wearable device in which the device was integrated was worn on a live subject's forearm. Besides, the wearable device was removed, put on a static surface, as well as tested by putting the wearable device on a non-live object held by a human subject. The tests have shown that the device determined the presence of a live tissue in 95% of cases when the wearable device in which the device was integrated was worn on a subject's forearm, and did not determine the presence of a live tissue in cases where the wearable device was removed from the subject's forearm, or was lying on a static surface. False determination of a live tissue occurred in no more than 4% of cases.

Thus, the possibility of implementing the intended use of the disclosure (live subject tissue detection) and the achievement of the technical result (highly accurate and fast detection of a live subject tissue) was confirmed.

It should be noted that the live subject tissue detection device and method are suitable for use, in particular, in wearable devices, such as the aforementioned smart watch, electronic rings, electronic bracelets, specialized wearable computers for athletes, divers, etc., and achieve the following advantageous effects. Alongside with the capability of identification of presence/absence of a live subject tissue (liveness) in its capacity as such, and determination of some vital signs of the subject, such as heart rate (HR) and blood pressure, the disclosure is efficient in applications which necessitate a quick determination as to whether the wearable device is worn on a subject's forearm or has been taken off E.g., depending on whether the wearable device is worn on a subject's forearm or taken off, it may stay logged in on a user account or log off. This may be used, e.g., in applications related to online banking, payment systems, etc., improving the safety of using such applications since the wearable device almost immediately logs off from the related user account as soon as it detects that the device has been taken off from the user's forearm.

Those skilled in the art shall understand that only some of the possible examples of techniques and material and technical means, by which the embodiments of the disclosure may be implemented, are described above and illustrated in the drawings. The detailed description of embodiments of the disclosure provided above is not intended for restricting or defining the scope of legal protection of the disclosure.

Other embodiments of the disclosure, which may be encompassed by the scope of the disclosure, may be conceived by those skilled in the art after careful reading of the above specification with reference to the accompanying drawings, and all such apparent modifications, changes and/or equivalent substitutions are deemed to be encompassed by the scope of the. All prior art cited and discussed herein are hereby incorporated in this specification by reference where applicable.

While the disclosure has been shown and described with reference to various embodiments thereof, it will be understood by those skilled in the art that various changes in form and details may be made therein without departing from the spirit and scope of the disclosure as defined by the appended claims and their equivalents.

The invention claimed is:

1. A live subject tissue detection device, comprising:
   a light source configured to emit light onto a tissue of a subject;
   a photodetector configured to:
      receive light reflected from the tissue of the subject and light reflected from blood flow of the subject, wherein the light reflected from the blood flow of the subject has a Doppler shift relative to the light reflected from the tissue of the subject, and
      generate a high frequency Doppler signal based on the Doppler shift; a detection circuitry configured to:
      receive the high frequency Doppler signal from the photodetector, and
      convert the high frequency Doppler signal into a low frequency signal; and
   at least one processor configured to:
      compute parameters of the low frequency signal,
      compare the parameters of the low frequency signal to respective reference values, and
      determine a presence of live subject tissue based on the comparison,
      wherein the comparing of the parameters of the low frequency signal to the respective reference values comprises splitting the low frequency signal into a plurality of spectral bands and comparing signal power levels in each of the plurality of spectral bands with the respective reference values.

2. The device of claim 1, wherein the detection circuitry comprises an analog-to-digital converter configured for analog-to-digital conversion of the high frequency Doppler signal.

3. The device of claim 1, wherein the detection circuitry is further configured to mix light reflected from the tissue and light reflected from the blood flow.

4. The device of claim 1, wherein the detection circuitry further comprises a low-pass filter.

5. The device of claim 1, wherein the detection circuitry further comprises a high-pass filter.

6. The device of claim 1, wherein the detection circuitry further comprises a band-pass filter.

7. The device of claim 1, wherein the light source comprises a coherent light source.

8. The device of claim 7, wherein the coherent light source comprises a laser diode.

9. The device of claim 1, wherein the photodetector comprises a photo diode or a heterodyne detector.

10. The device of claim 1, further comprising one or more lenses configured to provide penetration of the emitted light to a specified depth into the tissue.

11. A wearable user device comprising a live subject tissue detection device according to claim 1.

12. The device of claim 1, further comprising calculating a direct current level of signal (DC level) for the low frequency signal and comparing the signal DC level with the respective reference values.

13. A live subject tissue detection method, comprising:
   emitting light onto tissue of a subject;
   receiving light reflected from the tissue and light reflected from blood flow of the subject, wherein the light reflected from the blood flow has a Doppler shift relative to the light reflected from the tissue;
   generating a high frequency Doppler signal based on the Doppler shift;
   converting the high frequency Doppler signal into a low frequency signal;
   computing parameters of the low frequency signal;
   comparing the parameters of the low frequency signal to respective reference values; and determining a presence of live subject tissue based on the comparison, wherein the comparing of the parameters of the low frequency signal to the respective reference values comprises splitting the low frequency signal into a plurality of spectral bands and comparing signal power levels in each of the plurality of spectral bands with the respective reference values.

14. The method of claim 13, further comprising:

in response to determining that the live subject tissue is present, remaining logged in to a user account.

15. The method of claim 13, further comprising:

in response to determining that the live subject tissue is not present, logging out of a user account.

16. The method of claim 13, wherein the converting of the high frequency Doppler signal into the low frequency signal comprises performing an analog-to-digital conversion of the high frequency Doppler signal into the low frequency signal.

17. The method of claim 16, wherein the analog-to-digital conversion of the high frequency Doppler signal comprises generating an envelope of the high frequency Doppler signal.

18. The method of claim 16, wherein the converting of the high frequency Doppler signal into a low frequency signal comprises at least one of:

performing a high-pass filtering on the high frequency Doppler signal;

performing a low-pass filtering on the high frequency Doppler signal; or performing a band-pass filtering on the high frequency Doppler signal.

19. The method of claim 13, wherein the high frequency Doppler signal is obtained by mixing light reflected from the tissue and light reflected from the blood flow.

20. The method of claim 13, further comprising:

calculating a direct current level of signal (DC level) for the low frequency signal and comparing the signal DC level with the respective reference values.

* * * * *